United States Patent
Sohn et al.

(10) Patent No.: US 11,383,241 B2
(45) Date of Patent: Jul. 12, 2022

(54) MECHANO-NODE PORE SENSING

(71) Applicant: The Regents of the University of California, Oakland, CA (US)

(72) Inventors: Lydia L. Sohn, Berkeley, CA (US); Junghyun Kim, Berkeley, CA (US); Sewoon Han, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 178 days.

(21) Appl. No.: 16/382,190

(22) Filed: Apr. 11, 2019

(65) Prior Publication Data
US 2019/0240666 A1  Aug. 8, 2019

Related U.S. Application Data

(63) Continuation of application No. PCT/US2017/056423, filed on Oct. 12, 2017.

(60) Provisional application No. 62/571,255, filed on Oct. 11, 2017.

(51) Int. Cl.
| | |
|---|---|
| *B01L 3/00* | (2006.01) |
| *G01N 27/327* | (2006.01) |
| *G01N 27/403* | (2006.01) |
| *G01N 15/10* | (2006.01) |
| *G01N 33/487* | (2006.01) |

(52) U.S. Cl.
CPC .... *B01L 3/502761* (2013.01); *G01N 15/1031* (2013.01); *G01N 15/1056* (2013.01); *G01N 27/3275* (2013.01); *G01N 27/403* (2013.01); *G01N 33/48728* (2013.01); *B01L 3/502746* (2013.01); *G01N 2015/1006* (2013.01); *G01N 2015/1087* (2013.01); *G01N 2015/1093* (2013.01)

(58) Field of Classification Search
CPC ........ B01L 3/502761; B01L 3/502746; G01N 15/1031; G01N 33/48728; G01N 27/3275; G01N 27/403; G01N 15/1056; G01N 2015/1006; G01N 2015/1087; G01N 2015/1093; G01N 15/1484
See application file for complete search history.

(56) References Cited

U.S. PATENT DOCUMENTS

| 2014/0299521 A1* | 10/2014 | Sohn | B01L 3/502761 |
| | | | 209/571 |
| 2015/0140596 A1* | 5/2015 | Mak | G01N 33/5005 |
| | | | 435/29 |
| 2016/0193605 A1* | 7/2016 | Sharei | C12N 5/0634 |
| | | | 435/6.1 |

FOREIGN PATENT DOCUMENTS

WO   WO-2016004101 A1 *  1/2016  ....... G01N 33/56972

OTHER PUBLICATIONS

Balakrishnan et al. (K Balakrishnan, G Anwar, M Chapman, T Nguyen, A Kesavaraju, L Sohn, Node-pore sensing: a robust, high-dynamic range method for detecting biological species, Lab Chip 13 (2013) 1302-1307) (Year: 2013).*

Balakrishnan et al. (K Balakrishnan, J Whang, R Hwang, J Hack, L Godley, L Sohn, Anal. Chem. 87 (2015) 2988-2995) (Year: 2015).*

(Continued)

*Primary Examiner* — Joshua L Allen
(74) *Attorney, Agent, or Firm* — Richard Aron Osman

(57) ABSTRACT

Mechano-node-pore sensing (mechano-NPS), is a rapid, multi-parametric cell screening method that simultaneously quantifies cell diameter, transit time through a contraction channel, transverse deformation under constant strain, and recovery time after deformation.

10 Claims, 7 Drawing Sheets

(56) References Cited

OTHER PUBLICATIONS

Babahosseini et al. (H. Babahosseini, V. Srinivasaraghavan, M. Agah, Microfluidic chip bio-sensor for detection of cancer cells, Sensors, 2012 IEEE, 2012, pp. 1-4) (Year: 2012).*

Adamo et al. (A Adamo, A Sharei, L Adamo, B Lee, S Mao, KF Jensen, Microfluidics-based assessment of cell deformability, Anal. Chem. 84 (2012) 6438-6443) (Year: 2012).*

Guo et al. (Q Guo, SP Duffy, K Matthews, AT Santoso, MD Scott, H Ma, Microfluidic analysis of red blood cell deformability, J. Biomechanics 47 (2014) 1767-1776) (Year: 2014).*

Handayani et al. (S Handayani, DT Chiu, E Tjitra, JS Kuo, D Lampah, E Kenangalem, L Renia, G Snounou, RN Price, NM Anstey, B Russel, High deformability of plasmodium vivax-infected red blood cells under microfluidic conditions, J. Infectious Diseases 199 (2009) 445-450) (Year: 2009).*

Myrand-Lapierre et al. (ME Mayrand-Lapierre, X Deng, RR Ang, K Matthews, AT Santoso, H Ma, Multiplexed fluidic plunger mechanism for the measurement of red blood cell deformability, Lab Chip 15 (2015) 159-167) (Year: 2015).*

Quinn et al. (DJ Quinn, I Pivkin, SY Wong, KH Chiam, M Dao, GE Karniadakis, S Suresh, Combined simulation and experimental study of large deformation of red blood cells in microfluidic systems, Annals of Biomedical Engineering 39(3) (2011) 1041-1050) (Year: 2011).*

Shelby et al. (JP Shelby, J White, K Ganesan, PK Rathod, DT Chiu, A microfluidic model for single-cell capillary obstruction by Plasmodium falciparum-infected erythrocytes, PNAS, 100(25) (2003) 14618-14622) (Year: 2003).*

Zheng et al. (Y Zheng, E Shojaei-Baghini, C Wang, Y Sun, Microfluidic characterization of specific membrane capacity and cytoplasm conductivity of single cell, Biosensors and Bioelectronics 42 (2013) 496-502) (Year: 2013).*

Hupert et al. (ML Hupert, JM Jackson, H Wang, MA Witek, J Kamande, MI Milowsky, YE Whang, SA Soper, Arrays of high-aspect ratio microchannels for high-throughput isolation of circulating tumor cells, Microsyst Technol 20 (2014) 1815-1825) (Year: 2014).*

Zografos et al. (K Zografos, F Pimenta, MA Alves, MSN Oliveira, Microfluidic converging/diverging channels optimized for homogeneous extensional deformation, Biomicrofluidics 10 (2016) 1-20) (Year: 2016).*

Yariv et al. (E Yariv, KD Dorfman, Electrophoretic transport through channels of periodically varying cross section, Physics of Fluids 19 (2007) 1-7) (Year: 2007).*

Zhou et al. (T Zhou, J Ge, L Shi, J Fan, Z Liu, SW Joo, Dielectrophoretic choking phenomenon of a deformable particle in a converging-diverging microchannel, Electrophoresis 39 (2018) 590-596) (Year: 2018).*

Laachi et al. (N Laachi, C Declet, C Matson, KD Dorfman, Nonequilibrium transport of rigid macromolecules in periodically constricted geometries, Physical Review Letters 98 (2007) 1-4) (Year: 2007).*

* cited by examiner

Fig. 3A-E.

MECHANO-NODE PORE SENSING

This application is a continuation of PCT/US17/56423; Filed: Oct. 12, 2017, which claims priority to U.S. 62/407,425; Filed: Oct. 12, 2016 and U.S. 62/571,255; Filed: Oct. 11, 2017.

This invention was made with government support under Grant Numbers CA182375 and CA190843 awarded by the National Institutes of Health. The government has certain rights in the invention.

INTRODUCTION

Cells derive their mechanical properties from the structure and dynamics of their intracellular components, including the cytoskeleton, cell membrane, nucleus, and other organelles—all of which, in turn, emerge from cell type-specific genetic, epigenetic, and biochemical processes. The ability to identify differences within a population of one cell type or different cells among heterogeneous populations, or to detect changes due to disease or environmental interactions all based on cellular mechanical properties has potentially important implications for cell and tissue biology and clinical metrics. As examples, metastatic potential[1, 2], cell-cycle[3, 4], differentiation state[5-10], the outcome of tissue self-organization[11], and infection with intracellular pathogens[12, 13] have all been shown to correlate with changes in cellular mechanics. Even the process of aging has been shown to affect the ability of cells within the vascular system and musculoskeletal system to recover from mechanical deformation[14]. Thus, methods to measure multiple cellular mechanical properties rapidly and accurately have tremendous potential as label-free research tools and diagnostics.

Atomic-force microscopy (AFM)[15-17] and micropipette aspiration[18, 19] are the gold standard for performing mechanical measurements on cells. These methods provide controlled loading conditions (e.g. stress relaxation and creep indentation) and quantify such cellular properties as elastic modulus and cortical tension. They are, however, burdened by slow throughput, capable of analyzing only just a few cells/hr[7, 20], although recent adaptations of both methods have demonstrated higher throughput via more efficient analysis[21, 22]. Likewise, optical tweezers[23, 24] and microplate rheometery[25]—two other well-established methods to measure cellular mechanical properties—also suffer from low throughput. Given these drawbacks, a number of microfluidic platforms have consequently been developed, including hydrodynamic stretching cytometry[26-28], suspended microchannel resonators (SMR)[29], and real-time deformability cytometry (RT-DC)[30], to name only a few. Each of these methods, through optical imaging or measuring changes in resonant frequencies, can analyze populations of cells in a relatively short time (e.g. 2,000~65,000 cells/s for hydrodynamic stretching cytometry[26-28], 30 cells/s for SMR[29], and 100 cells/s for RT-DC[30]). To identify specific cell types, these methods most often focus on correlating cell size or mass with a specific mechanical property. For example, hydrodynamic stretching cytometry and RT-DC compare cellular deformability with cell size, and SMR determines the transit time of cells through a narrow channel with respect to cell mass. Populations of cells are complex with respect to the continua of cell states that are represented within, and as such, multiple biophysical parameters are necessary to deconvolve and identify complex cellular mixtures. Recently, Masaeli et al.[31] and Lin et al.[31, 32] have reported using deformability cytometry to measure multiple parameters, such as cell size, morphology, and relaxation rate, while cells undergo deformation. In so doing, they were able to identify different cellular states associated with pluripotent and neural stem-cell differentiation, respectively. While this achievement emphasizes the need for measuring multiple biophysical parameters to identify specific cell types, Masaeli et al.[31] and Lin et al.[31, 32] focus on defining cellular phenotypes only while cells undergo deformation. Since overall recovery of a cell once released from deformation plays significant roles in cellular migration processes such as cancer metastasis[33] and in providing a protective mechanism of cells against mechanical damage[34-36], it is imperative for mechano-phenotyping platforms to have a temporal window sufficient enough to analyze the recovery that a cell undergoes after deformation.

Here, we describe a novel microfluidic platform called "mechano-Node-Pore Sensing" (mechano-NPS). Mechano-NPS involves integrating a node-pore sensor[37, 38] with a contraction channel and performing a four-terminal measurement of the current across the integrated microfluidic channel to quantify four biophysical properties of a single cell, simultaneously: diameter, resistance to compressive deformation, transverse deformation, and recovery from deformation. This electronic-based method of multi-dimensional mechanical phenotyping provides the means to use these biophysical parameters as label-free biomarkers for identification and differentiation among cell types and, uniquely, to determine the effects of chronological age and malignant progression on cell elasticity and recovery from deformation. Mechano-NPS distinguishes malignant from non-malignant immortal cells and measures deformability changes in the cytoskeleton. In addition, mechano-NPS can discriminate between sub-lineages and among chronological age groups of primary normal human based solely on their mechanical properties. Mechano-NPS represents an efficient, simple, and direct means to quantify multiple mechanical properties of single cells in heterogeneous populations.

SUMMARY OF THE INVENTION

The invention provides devices and methods of mechanical phenotyping of cells.

In one aspect the invention provides a mechano-node-pore sensor (mechano-NPS) comprising a node-pore sensor operably connected to a microfluidic contraction channel.

In embodiments:

the mechano-node-pore sensor comprises an outer pair of electrodes configured to supply a voltage across the channel, and an inner pair of electrodes configured to measure changes in current across the channel;

the mechano-node-pore sensor is configured to provide a multi-terminal measurement of current across the channel to quantify multiple biophysical properties of a single cell transiting the channel, preferably simultaneously, including two, three or four of: diameter, resistance to compressive deformation, transverse deformation, and recovery from deformation;

the channel is a sinusoidal contraction channel configured to induce periodic deformation to probe cellular viscoelastic properties, which depend non-linearly on the frequency of deformation; and/or the mechano NPS is integrated with a functionalized channel, such as affinity coatings, see, e.g. U.S. Pat. No. 9,719,991, to detect cell surface interations, such as wherein a portion of the channel is functionalized before or after the node-pore and comprises an affinity coating comprising affinity reagents such as antibodies, aptamers, glycoproteins, etc., specific for cell surface markers or epitopes.

The invention provides methods, including methods of using a mechano-node-pore sensor to obtain a whole-cell deformability index (wCDI), which normalizes the effects of cell diameter with respect to the whole-cell deformability;

methods of using a mechano-node-pore sensor to measure a single cell's diameter, transit time, transverse deformation, and/or recovery from deformation, preferably simultaneously;

methods of using a mechano-node-pore sensor in a multidimensional method of mechanical phenotyping providing biophysical parameters as label free biomarkers for cellular identification and/or determining effects of chronological age or malignant progression on cell elasticity and recovery from deformation;

methods of using a mechano-node-pore sensor with signal processing and real-time analysis; and/or methods of using a mechano-node-pore sensor comprising measuring with the sensor a single cell's diameter, transit time, transverse deformation, and/or recovery from deformation to screen in performing drug screening or assaying effects of drugs in vitro cell assays, in determining predicting a response to a particular therapy in personalized medicine applications, or in a label-free process of tracking to track cells in culture.

The invention encompasses all combination of the particular embodiments recited herein, as if each combination had been laboriously recited.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

The mechanical properties of cells change with their differentiation, chronological age, and malignant progression. Consequently, these properties may be useful label-free biomarkers of various functional or clinically relevant cell states. Here, we demonstrate mechano-node-pore sensing (mechano-NPS), a multi-parametric single-cell-analysis method that utilizes a four-terminal measurement of the current across a microfluidic channel to quantify simultaneously cell diameter, resistance to compressive deformation, transverse deformation under constant strain, and recovery time after deformation. We define a new parameter, the whole-cell deformability index (wCDI), which provides a quantitative mechanical metric of the resistance to compressive deformation that can be used to discriminate among different cell types. The wCDI and the transverse deformation under constant strain show malignant MCF-7 and A549 cell lines are mechanically distinct from non-malignant, MCF-10A and BEAS-2B cell lines, and distinguishes between cells treated or untreated with cytoskeleton-perturbing small molecules. We categorize cell recovery time, $\Delta T_r$, as instantaneous ($\Delta T_r \sim 0$ ms), transient ($\Delta T_r \leq 40$ ms), or prolonged ($\Delta T_r > 40$ ms), and show that the composition of recovery types, which is a consequence of changes in cytoskeletal organization, correlates with cellular transformation. Through the wCDI and cell-recovery time, mechano-NPS discriminates between sub-lineages of normal primary human mammary epithelial cells with accuracy comparable to flow cytometry, but without antibody labeling. Mechano-NPS identifies mechanical phenotypes that distinguishes lineage, chronological age, and stage of malignant progression in human cells.

Population Characterization of Mechanical Phenotypes at Single-Cell Resolution

Experimental Design

Figures 1A, 1B, 1C, 1D:
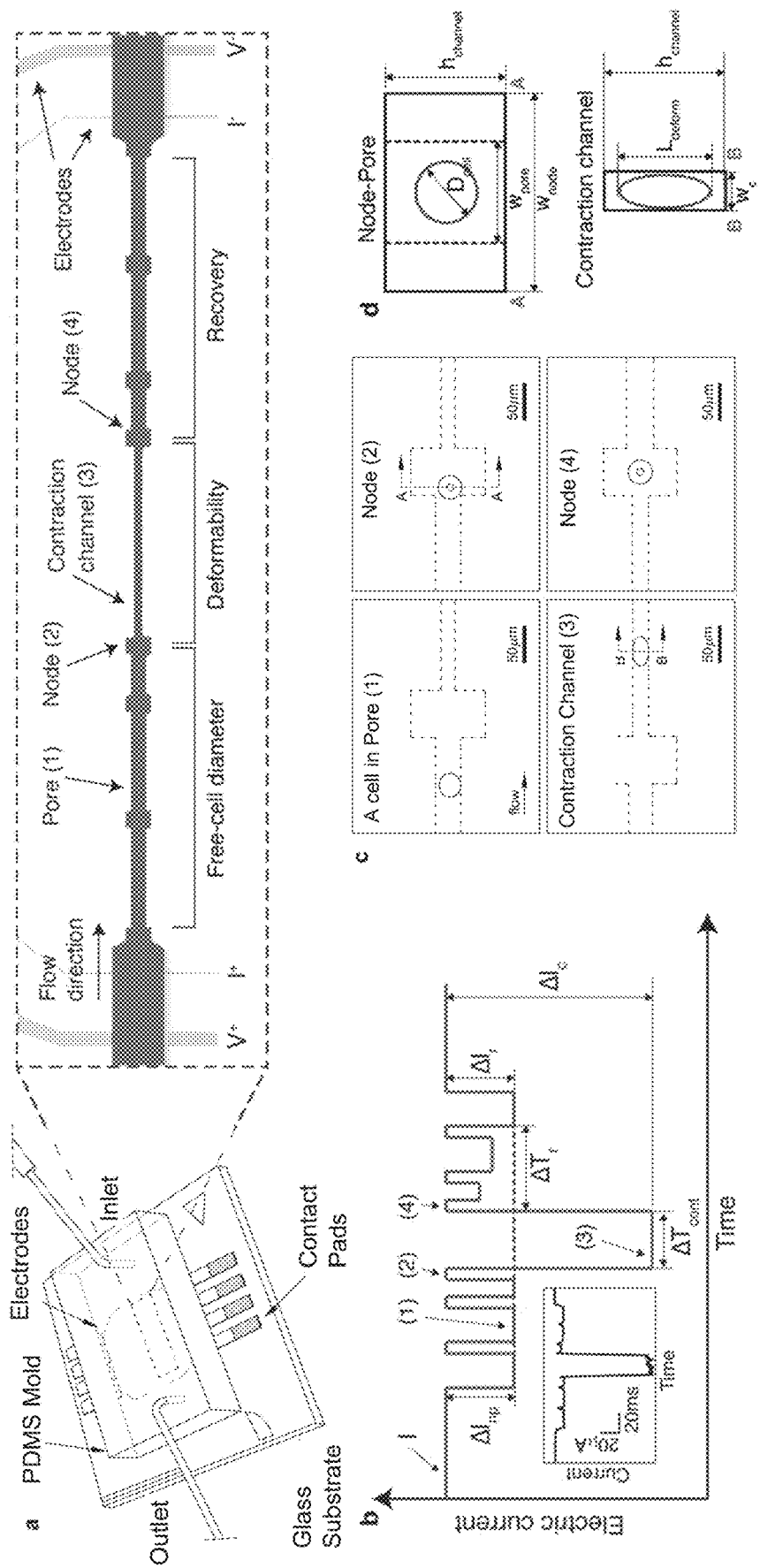
FIG. 1A-1D. Principle of mechanical phenotyping via mechano-NPS. a, A photographic image of the microfluidic platform. b, Expected current pulse generated by a cell transiting the microfluidic channel. c, Time-snapshots of an MCF-7 cell (bordered by a white circle) in each of the different segments of the microfluidic channel (white dashed line). d, Cross-sectional diagram of the channel segments occupied by a cell.
Figure 2:
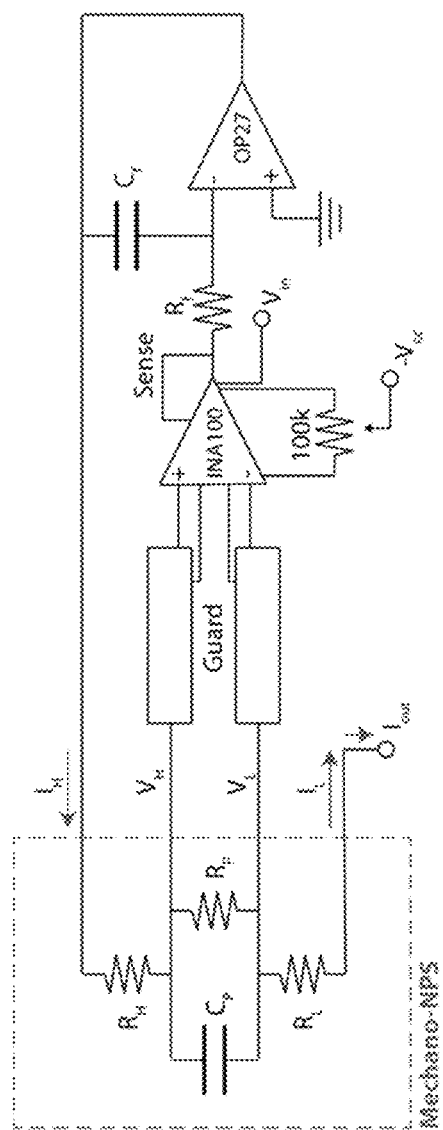
FIG. 2. The electrical circuit model for the constant voltage four-point measurement FIG. 3A-E. Signal processing by customized MATLAB code. The acquired signal a, is first low-pass filtered b, to remove noise. The base-line is then normalized c, to remove any drift. d, A derivative cut-off detection is subsequently employed as an index to determine the start and end point of each pulse. e, Finally, the current pulse magnitude and duration are measured based on this index.
Figure 3:

Platform design, including geometry and sizing, may be configured and adapted to target indications, such as cell type and size range. In this example, the platform comprises of a 30 µm-high microfluidic channel embedded in a polydimethylsiloxane (PDMS) mold bonded to a glass substrate with pre-defined platinum (Pt) electrodes and gold (Au) contact pads (FIG. 1a). The central part of the channel, which we refer to as the "contraction channel", is long (2055 µm) and narrow (10 or 12 µm-wide) and flanked on either side by a series of nodes and pores that are 85 µm and 25 µm wide, respectively (FIG. 1a, inset). The length of the contraction channel was chosen to provide sufficient time (~30 ms) over which a cell experiences constant applied strain. The node and pore dimensions were chosen for sufficient signal-to noise ratios. Given the flexibility and ease of device design and fabrication, different contraction channel lengths and node and pore dimensions could be employed. Filters that are 25 µm in width (the width chosen based on the size range of cells measured in these studies, ~15-20 µm in diameter) are included at the entrance of the microfluidic channel in order to remove cellular clusters that may otherwise clog the device. Applying a constant DC voltage (1 V) across the channel, we employ a four-terminal measurement technique[37-40] to measure the current pulses caused by cells transiting across the microfluidic channel when a non-pulsatile pressure of ~21 kPa (determined by a commercial pressure gauge, SSI Technologies) is utilized (FIG. 1b and FIG. 2). After low-pass filtering all current versus time data, we employ custom-written software to extract both the magnitude and duration of each current sub-pulse ($\Delta I_{np}$, $\Delta I_c$, $\Delta T_{cont}$, and $\Delta T_r$ in FIG. 1b; FIG. 3).

Figure 4:
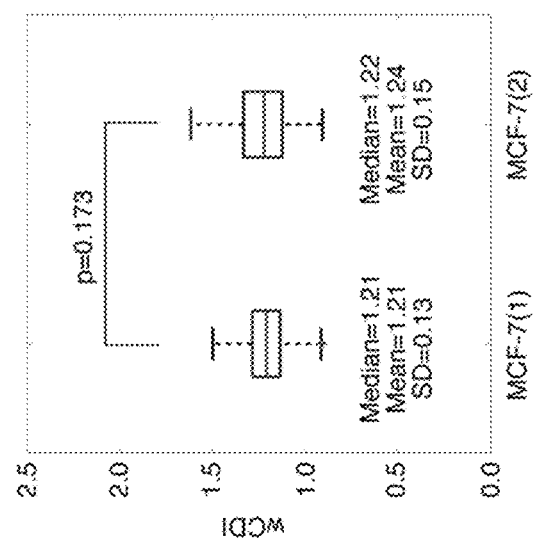
FIG. 4. wCDI of MCF7 cells from different replicas of the mechano-NPS device.

Power analysis was employed to ensure that our sample size for mechanical phenotyping offers adequate power (≥0.80) to detect differences between experimental groups within a 95% confidence interval[41] from the measured data set. For all cases which have a p-value <0.05, the analyzed sample size ($N_a$) provided sufficient power value to measure statistical differences. Statistical significance was determined by performing a paired t-test or chi-square test. To ensure repeatability of results, all data presented in this study were measured using multiple microfluidic devices. The wCDI of MCF-7 cells obtained with different device replicas showed no statistical difference (FIG. 4, p=0.173).

Device Fabrication

The devices may be fabricated from a variety of materials that provide the requisite structural and chemical properties, including molded polymers/plastics, ceramics and etched glasses. For example, to make the PDMS molds of our microfluidic platform, we employ standard soft-lithography. Briefly, we fabricate negative-relief masters onto polished silicon wafers. After mixing and degassing, we pour a 9:1 pre-polymer:curing agent mixture of PDMS (Sylgard 184, Dow Corning) onto the masters and subsequently cure them at 80° C. for 60 minutes. A slab of PDMS with the embedded microfluidic channel is excised from the master, and entry and exit ports are cored with a 1 mm diameter biopsy punch. To complete the device, we first expose the PDMS mold and a glass substrate with pre-defined electrodes to an oxygen plasma (470 mTorr, 80 W, 1 min), then align and mate the two together, and finally place the device onto a hotplate set to 80° C. for 60 minutes. For the specific surface-treatment experiments described, we injected either Poly-D-lysine (PDL, 1 µg/mL in PBS) or bovine serum albumin (BSA, 2% w/v in PBS) into the completed device. After incubating for 2 hours at 37° C., we flushed the device with PBS and immediately began screening cells.

To fabricate the Pt electrodes and the Au contact pads onto glass substrates, we utilize standard photolithography for patterning. Using electron-gun evaporation, we deposit a 75/250/250 Å Ti(Titanium)/Pt/Au thin film onto the patterned substrates. We then use a gold wet etch (GOLD ETCHANT TFA, Transene Company) to expose the Pt electrodes.

Cell Culture

MCF-10A cells (ATCC® CRL-10317™) were cultured in MEBM medium, supplemented with 0.1% insulin, 0.1% hEGF, 0.4% hydrocortisone, and 10% cholera toxin. MCF-7 cells (ATCC® HTB-22™) were cultured in DMEM (Fisher Scientific, BW12719F), supplemented with 10% fetal bovine serum (FBS), 0.1 mM MEM Non-Essential Amino Acids (NEAA), 2 mM L-glutamine, and 1% Pen-Strep. BEAS-2B cells (ATCC® CRL-9609™) were cultured in BEGM BulletKit (Lonza, CC-3170). A549 cells (ATCC® CRM-CCL-185™) were cultured in F-12K medium (Fisher Scientific, MT10025CV), supplemented with 10% FBS and 1% of Pen-Strep. Jurkat cells (ATCC® TIB-152™) were cultured in RPMI 1640 medium (Thermo Scientific, 88421), supplemented with 10% fetal bovine serum (FBS), and 1% Pen-Strep. All cell cultures were maintained at 37° C. in 5% $CO_2$ and routinely passaged, per published protocols[42, 43], once they reached 80% confluence.

Cells were dissociated by treatment with 0.25% trypsin/EDTA for either 3 min (MCF-7 and A549 cells) or 5 min (MCF-10A and BEAS-2B cells) at 37° C.[44-46], washed with the respective growth media, centrifuged at 0.2 RCF, and re-suspended at a concentration of ~20,000 cells/mL in PBS. To ensure cell viability, cells were injected into the prepared devices for screening immediately following re-suspension.

Primary Human Mammary Epithelial Cells (HMECS)

Primary HMEC strains were generated and maintained as described previously[47, 48]. HMECs were grown in M87A medium containing cholera toxin and oxytocin at 0.5 ng/mL and 0.1 nM, respectively. Details on the derivation and culture of these HMEC can be found at Human Mammary Epithelial Cell (HMEC) Bank Website[49]. Research was conducted under Lawrence Berkeley National Laboratory Human Subjects Committee IRB protocols 305H002 and 108H004 which allows for the use of HMEC samples for future scientific research.

Pharmacological Inhibition of Cytoskeletal Components

We disrupted actin polymerization with Latrunculin A and B (LatA and LatB, Enzo Life Sciences)[50]. Prior to deformability measurements, MCF-7 and MCF-10A cells were incubated with 2.5 or 5 µg/mL LatA or LatB in each cell's respective growth medium for one hour at 37° C. and 5% $CO_2$[29, 51, 52]. Cells were then released from culture flasks with 0.25% trypsin/EDTA, rinsed once with PBS, centrifuged at 0.2 RCF, and re-suspended in PBS at a concentration of ~100,000 cells/mL. To confirm that actin polymerization was successfully inhibited after incubation, cells were fixed by 4% (w/v) paraformaldehyde in PBS for 15 min. They were then permeabilized with 0.1% Triton-X 100 (Sigma-Aldrich) in PBS for 5 min. Cell nuclei and F-actin were then counter-stained with 4',6-diamidino-2-phenylindole (DAPI, Sigma-Aldrich, 10236276001) and rhodamine phalloidin (Thermo Fisher Scientific, R415), respectively, per manufacturer's protocol, and then imaged with a Zeiss LSM710 confocal microscope.

Discriminating Cell Types Based on the Whole Cell Deformability Index (wCDI)

We derived a dimensionless parameter, which we refer to as the whole cell deformability index (wCDI), to distinguish cell populations based on mechanical phenotype. We assume a functional relationship among the biophysical parameters of a cell and fluid flow as follows, $$F(E, D_{cell}, h_{channel}, U_{flow}, \Delta T_{cont}, \mu, L_c) = 0 \qquad (1)$$

where E, $D_{cell}$, $h_{channel}$, $U_{flow}$, $U_c$, $\mu$, and $L_c$ correspond to elastic modulus, free cell diameter, height of the microfluidic channel, flow velocity within the node segment leading to the contraction channel, the transit velocity of cells in the contraction channel, fluid viscosity, and the length of the contraction channel, respectively. Three fundamental dimensions (n=3)—mass (M), length (L), and time (T)—are included in each of these six parameters (n'=7) as follows, $$E = [ML^{-1}T^{-2}] \quad (2a)$$

$$D_{cell} = [L] \quad (2b)$$

$$h_{channel} = [L] \quad (2c)$$

$$U_c = [LT^{-1}] \quad (2d)$$

$$U_{flow} = [LT^{-1}] \quad (2e)$$

$$\mu = [ML^{-1}T^{-1}] \quad (2f)$$

$$L_c = [L] \quad (2g)$$

Following the Buckingham π theorem[53], the relationship among these parameters can be written in terms of a set of four dimensionless parameters (n'−n=4). To find these dimensionless parameters ($\pi_i$; i=1, 2, 3, and 4), we select repeating variables ($h_{channel}$, $U_{flow}$, and $\mu$), where the number of required variables is equal to the number of fundamental dimensions (n=3). Multiplying one of the nonrepeating variables with the product of the repeating variables, we can define the following π terms, $$\pi_1 = \frac{h_{channel} E}{U_{flow} \mu} \quad (3a)$$

$$\pi_2 = \frac{h_{channel}}{\Delta T_{cont} U_{flow}} \quad (3b)$$

$$\pi_3 = \frac{D_{cell}}{h_{channel}} \quad (3c)$$

$$\pi_4 = \frac{L_i}{h_{channel}} \quad (3d)$$

We define the dimensionless parameter, wCDI (Equation (6)), to be the product of $\pi_2 \times \pi_3 \times \pi_4$. The wCDI could also be defined as a function of $\pi_1$, in which ($\pi_1 = f(\pi_2, \pi_3, \pi_4)$), but the exact analytical expression can only be determined by experiment[53]. Comparing the wCDI with cellular cortical tension and the previously reported elastic modulus (E) of various cell lines (FIG. 5), we experimentally determined that the wCDI is inversely related to these traditional parameters.

Cortical Tension Measurement Using Micropipette Aspiration

Cortical tension was measured by micropipette aspiration as described previously[54, 55]. Briefly, cells were trypsinized and resuspended in growth medium, and were transferred to the imaging chamber. Suction pressures in the range of 0.03 to 0.3 kPa were applied to the cells through an 8-10 μm glass micropipette. At each pressure, the cellular deformation inside the pipette was allowed to stabilize for 20-30 seconds before imaging. The average measurement from three images was used to calculate the length of deformation ($L_p$). Subsequently, applied pressure was increased in 0.03 kPa increments till the $L_p$ exceeded the radius of the pipette ($R_p$). Any cell that blebbed was discarded. The critical pressure ($P_{crit}$) is defined as the pressure at which the deformation inside the pipette is hemispherical, i.e. $L_p = R_p$. The cortical tension ($T_{eff}$) was then calculated using the following equation, where $R_c$ is:

$$\Delta P_{crit} = 2T_{eff} * \left( \frac{1}{R_p} - \frac{1}{R_c} \right) \quad (4)$$

The cortical tension measurements from Jurkat, NIH 3T3, and HeLa cells are plotted from Schiffhauer et al. 2016[56].

Results

Population Characterization of Mechanical Phenotypes at Single-Cell Resolution

Figure 6:
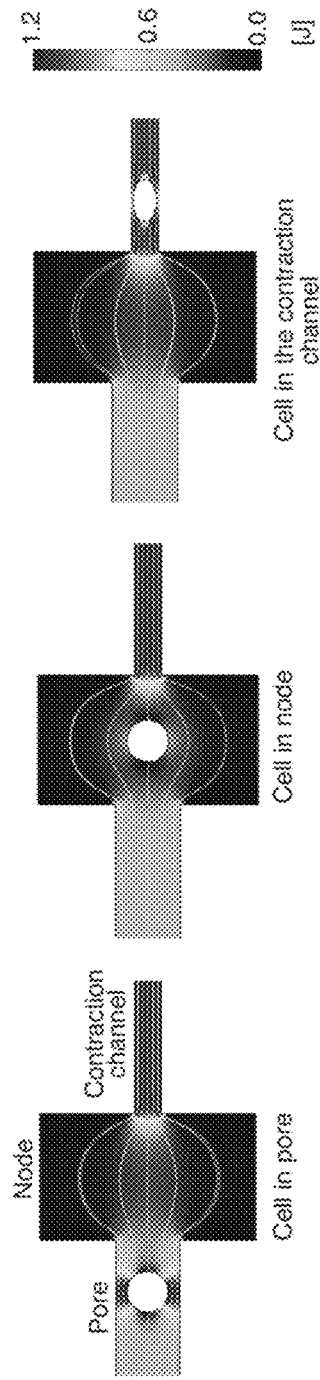
FIG. 6. Computational modeling of the electric field when a cell transits each section of the mechano-NPS microfluidic channel.

The repeated expansion and contraction of the width of our overall microfluidic channel shown in FIG. 1a produces a unique and symmetric current pulse, consisting of sub-pulses, for each cell that transits the channel. Upon entering the microfluidic channel, a cell partially blocks the flow of current, and consequently, the measured current immediately drops from a baseline value, I (FIG. 1b). When the cell enters the first node, the current returns to baseline only to drop again once the cell exits that node. This is a hallmark of node-pore sensing (NPS)[37, 38]. The rise and fall of current repeats as the cell enters and exists the next two nodes. Upon entering the contraction channel where the width is narrower than the diameter of the cell, the cell deforms as shown in FIGS. 1c and d. Because the cell blocks nearly all of the current flow in this part of the channel, the current drop from baseline is far more dramatic than that resulting from the cell transiting the earlier pores (FIG. 6). The cell subsequently enters and exits a series of node-pore pairs following the contraction channel, ultimately leading to the symmetrical shape of the overall current pulse. This symmetry is intentional by design and critically allows the monitoring of a cell's recovery from constant strain deformation.

The magnitude of the current sub-pulse produced in the node-pore sequence ($\Delta I_{np}$) and the contraction channel ($\Delta I_c$) corresponds to the free-cell diameter ($D_{cell}$) and cell elongation length ($L_{deform}$), respectively (FIG. 1d). The relationship among the current drop ($\Delta I$), baseline current (I), particle diameter (d), the overall channel length (L) and the channel's effective diameter ($D_e$) is defined as[39, 57, 58], $$\frac{\Delta I}{I} = \frac{d^3}{D_e^2 L} \left[ \frac{1}{1 - 0.8(d/D_e)^3} \right] \quad (5)$$

To determine $D_e$, we measure polystyrene microspheres of known size with the microfluidic channel. Using the values of $\Delta I/I$ arising from the microspheres, along with the known values of L and d (the size of the microspheres in this instance), we can numerically solve for $D_e$ in Equation (5). Once $D_e$ is known, we can subsequently determine $D_{cell}$ of a screened cell by numerically solving for d in Equation (5) using the obtained values of $\Delta I_{np}/I$. We can also determine the volume of the deformed cell, $V_{deform}$, by the relationship[39, 57, 58], $\Delta I_c/I \sim V_{deform}/V_{contraction}$, where $V_{contraction}$ is the volume of the contraction channel. To calculate $L_{deform}$, we assume the cell undergoes an isometric deformation in the direction of both the channel's longitudinal axis and channel height, resulting in an oblate-spheroid shape. From the relationship between the volume and major radius of the oblate spheroid, $V_{deform} = \pi w_c L_{deform}^2 / 6$ where $w_c$ is the contraction-channel width, we can determine $L_{deform}$ from $\Delta I_c/I$. We quantify the transverse deformation of the cell, $\delta_{deform} = L_{deform}/D_{cell}$, as it transits the contraction channel.

As a cell traverses through each section of the channel, the duration of the resulting sub-pulse produced by a cell corresponds to the cell's transit time ($\Delta T$) through that part of the channel. To quantify the resistance to compressive deformation, we utilize $\Delta T_{cont}$. To determine the recovery time of a cell from compressive deformation ($\Delta T_r$), we note the time required for the sub-pulses produced by the cell after exiting the contraction channel to return to the same shape and magnitude as those produced by the cell prior to entering the contraction channel, i.e. when the cell returns to its original size and shape (FIG. 1b; FIG. 7). Given the number of node-pore pairs and the overall length of the node-pore sequence we employ after the contraction channel, our device's temporal window for measuring cell recovery is 40 ms. The flexibility of our device design and ease of fabrication allow for the inclusion of many more node-pore pairs after the contraction channel, which in turn would lead to an increase in time over which to observe recovery. Based on all the recovery times we recorded with our particular device, we discriminate among three different cell-recovery types—instant ($\Delta T_r$~0 ms), transient ($0<\Delta T_r \leq 40$ ms), and prolonged ($\Delta T_r > 40$ ms) (FIG. 7).

Thus, from just a single current pulse produced by a cell transiting through the entire microfluidic channel, four biophysical properties of that cell—size ($D_{cell}$), resistance to compressive deformation ($\Delta T_{cont}$), transverse deformation ($\delta_{deform}$), and recovery from deformation ($\Delta T_r$)—are extracted. These parameters are what we collectively use to mechanically phenotype a single cell, distinguish among cell types in a heterogeneous population, and determine subtle cellular changes.

Distinguishing Malignant and Non-Malignant Epithelial Cell Lines Based on Mechanical Phenotyping We investigated whether mechano-NPS could distinguish between immortal malignant and non-malignant states in two different epithelial tissue types based on their mechanical properties alone. We compared the mechanical properties of malignant MCF-7 with non-malignant MCF-10A breast epithelial cells and malignant A549 with non-malignant BEAS-2B lung epithelial cells when individual cells were subjected to a constant applied strain along the length of the contraction channel they traversed. Because strain, $\varepsilon$, is a function of both cell size and contraction channel width ($w_c$), $\varepsilon = (D_{cell} - w_c)/D_{cell}$, and prior independent measurement of $D_{cell}$ showed that malignant MCF-7 and A549 cells are, on average, larger than non-malignant MCF-10A and BEAS-2B cells, we utilized a 12 μm-wide contraction channel to measure MCF-7 and A549 cells and a 10 μm-wide contraction channel to measure MCF-10A and BEAS-2B in order to achieve the same average $\varepsilon$ (~0.3) for all cell types. As shown in four dimensional (4D) graphs, $D_{cell}$ and $L_{deform}$ of MCF-10A and BEAS-2B cells are significantly different from those of MCF-7 and A549 cells, respectively. Moreover, MCF-10A and BEAS-2B cells transit the contraction channel more slowly as compared to MCF-7 and A549 cells, respectively. When comparing transverse deformation ($\delta_{deform}$), we find that while A549 deform significantly less than BEAS-2B cells, MCF-7 and MCF-10A cells have similar deformation.

Although our results clearly show that the transit time through the contraction channel ($\Delta T_{cont}$) is dependent on cell type (i.e. malignant vs. non-malignant), so too could cell diameter affect transit time[59-61]. Because this could lead to difficulties in distinguishing cells within a heterogeneous population, we employ the Buckingham π-technique[53] to define a new dimensionless parameter, the whole-cell deformability index (wCDI), which relates $D_{cell}$ and $\Delta T_{cont}$ by the following:

$$wCDI = \frac{L_c}{U_{flow} h_{channel}} \cdot \frac{D_{cell}}{\Delta T_{cont}} \quad (6)$$

where $U_{flow}$ is the fluid velocity in the node section leading into the contraction channel, $L_c$ is the length of contraction channel, and $h_{channel}$ is the contraction-channel height (see detailed information in section: Discriminating cell types based on the whole cell deformability Index (wCDI)). $U_{flow}$, $L_c$, and $h_{channel}$ are fixed values for any given experiment, and consequently, $D_{cell}$ and $\Delta T_{cont}$ become the key parameters. Physically, the wCDI describes the deformability of the cell as a whole, including the cytoskeleton, nucleus, and organelles. Cells that are more deformable (i.e. less stiff) transit through the contraction channel more easily, and subsequently at higher velocities, than those that are less deformable (i.e. more stiff). Correspondingly, these cells will have a higher wCDI as compared to the latter, in accordance with Equation (6). Moreover, cells which are larger (smaller) will transit the contraction channel more slowly (quickly), and Equation (6) effectively negates this cell-size effect. While the Buckingham π-technique relates the wCDI to the cell's elastic modulus, E, (see Eq. 3a), it does not define the explicit relationship between the two. We, therefore, performed side-by-side measurements of different cell lines (Jurkat, MCF-7, and MCF-10A) with the gold standard, micropipette aspiration, and also compared our measurements of MCF-7, MCF-10A, A549, and BEAS-2B cell lines with those obtained by AFM in the published literature[15, 17, 62-67]. Our results and subsequent analysis (FIG. 5) show that the wCDI is inversely proportional to both cortical tension and E, confirming our original physical description of the wCDI. While future studies are necessary to determine the exact analytical expression between the wCDI and E, mechano-NPS's ability to mechanically phenotype cells successfully for cell-type discrimination is clearly demonstrated. The wCDI distribution of non-malignant vs. malignant cells showed that the wCDI of MCF-7 cells is significantly greater than that of MCF-10A cells with a 2.6% overlap. Similarly, A549 cells have a greater numerical wCDI than BEAS-2B cells, but with only a 1.6% overlap. Given the sensitivity demonstrated using the wCDI vs. $\Delta T_{cont}$ or cell size, alone, mechano-NPS and correspondingly the wCDI can be utilized as a method for detecting subtle heterogeneities within cell populations such as those found in primary tissue[68, 69], heterogeneous cell lines and strains[70], and biopsied tissue samples[71, 72].

Clear differences were observed in the recovery time after mechanical strain between breast and lung epithelial cell lines and, in the case of the latter, between malignant and non-malignant cell lines. There was no statistical difference (using a Chi-square Analysis) regarding instantaneous recovery from mechanical deformation among breast epithelial cells (38.3% malignant MCF-7 cells vs. 50% MCF10-A cells, p=0.101). This is in striking contrast to lung epithelial cells in which there was a strong statistical difference (p<0.0001) between malignant and non-malignant cell lines: 37.0% of malignant A549 cells recovered instantaneously vs. 82.0% of non-malignant BEAS-2B cells screened. Even though both are malignant cell lines, MCF-7 and A549 cell populations show surprising differences in their composition of transient and prolonged cell-recovery types. Whereas the majority of screened A549 cells transiently recovered (53.0%), MCF-7 cells were nearly evenly divided between transient and prolonged recovery (38.3% and 47.5%, respectively).

Evaluating the Contribution of Cell-Surface Interactions and the Cytoskeletal Component, F-Actin, to the Mechanical Phenotypes Measured To determine whether cell-surface interactions greatly affect the passage of a cell within the contraction channel, and in turn contribute significantly to its wCDI, we screened MCF-7 cells in channels coated with either poly-D-lysine (PDL) or bovine serum albumin (BSA) and compared the resulting wCDI with that obtained by screening with a bare-PDMS channel. PDL increases cell-surface interactions by adding positive charges on the PDMS channel walls[73, 74] and would therefore lead to a lower wCDI. In contrast, BSA inhibits cellular adhesion to the PDMS surface[75] and would result in a higher wCDI. We compared the wCDI obtained when MCF-7 cells were measured with bare-PDMS and PDL- and BSA-coated channels at different inlet pressures, i.e. flow speeds. At low pressures ($P_{inlet}$=7 kPa and 14 kPa), the average wCDI is appreciably lower in the PDL-coated channel and higher in the BSA-channel as compared to the bare-PDMS control channel. At $P_{inlet}$=21 kPa, the inlet pressure at which we performed all our experiments, cells flow at a sufficiently high enough rate that cell-surface interactions are minimized within the contraction channel. The obtained wCDI at this inlet pressure for either the PDL- or BSA-coated channel is not a dramatic shift from that measured with the bare-PDMS control channel. Moreover, the difference in wCDI among the different surface treatments vs. the bare-PDMS control channel at 21 kPa inlet pressure is significantly less than that measured between malignant and non-malignant epithelial cell types. We, therefore, conclude that while surface-interactions do contribute to the wCDI, they are not the dominant factor at the higher inlet pressures or flow rates used for these studies.

Because we propose that mechano-NPS distinguishes cells based on mechanical differences, we should detect cytoskeletal perturbations. Thus, we treated MCF-7 and MCF-10A cells with the actin polymerization inhibitors, Latrunculin A (LatA) or B (LatB), and subsequently screened them under a strain magnitude, $\varepsilon_{avg}$~0.3. We found that the cellular deformation in the transverse direction ($\delta_{deform}$) of both MCF-7 and MCF-10A cells treated with LatA and LatB was significantly reduced compared to their respective controls, with MCF-7 cells generally more so than MCF-10A cells. Furthermore, we found that the wCDI increased for both LatA- and LatB-treated MCF-7 cells, and for LatA-treated MCF-10A cells as compared to the untreated control cells. In subsequent experiments, we observed that the change in wCDI caused by LatA treatment correspondingly increased with concentration for both MCF-7 and MCF-10A cells, with the latter more sensitive to the treatment. This is in contrast, however, to no detectable change in wCDI of MCF-10A cells no matter the LatB concentration. Overall, the different response of MCF-7 and MCF-10A cells to LatA and LatB may be due to differences in F-actin content, but further experiments are warranted here. As we confirmed with staining and confocal microscopy that the F-actin filaments were indeed inhibited in the Lat A- and B-treated cells (more so with Lat-A than with Lat-B), we conclude that mechano-NPS successfully detects cytoskeletal perturbations induced by exogenous chemicals.

While differences between the wCDI of LatA-treated cells are more pronounced with MCF-10A cells than MCF-7 cells, the differences in recovery time for Lat A- and LatB-treated cells in both cell types vs. the control are far more significant. Latrunculin treatment results in the slow recovery of both MCF-7 and MCF-10A cells from the sudden relief of deformation. Moreover, there is a statistically significant difference between untreated and treated cells regarding recovery. In the case of MCF-7, only 8.1% of LatA-treated and 24.2% of LatB-treated cells instantaneously recover vs. 38.3% of untreated cells. For MCF-10A, the majority of LatA- and LatB-treated cells (66.7% and 41.4%, respectively) do not recover within the 40 ms time window our device offers (vs. 9.7% of untreated control cells). As we also found, the changes in cellular recovery are generally more pronounced at higher concentrations of Latrunculin treatment. These results support the notion that actin filaments contribute to the ability of cells to retain their original shape[36, 76]. Moreover, mechano-NPS detects differences in recovery from deformation, either transiently or not at all, between LatA- and LatB-treatment that are consistent with LatA being the more avid inhibitor of actin polymerization.

Mechanical Phenotyping of Human Mammary Epithelial Cells

To determine whether our platform could discriminate different lineages within a population of primary epithelial cells, we screened the mechanical phenotypes of HMECs, which broadly consist of two lineages: myoepithelial (MEP) cells and luminal epithelial (LEP) cells. MEP and LEP cells have distinct roles in breast tissue. MEP cells play active roles in ductal contraction and in tumor suppression, and LEP cells produce milk and may represent a target-cell-type for carcinogenesis[77]. Previous studies of mammary epithelia have implicated profound roles of cytoskeletal components in morphogenesis[11, 78, 79]. We measured the mechanical characteristics of these two lineages of cells. Since both MEP and LEP cells have a similar size range, we employed a 10 μm-wide contraction channel, corresponding to an $\varepsilon_{avg}$~0.4 for all measurements. Our data show the relationship among the measured parameters of MEP and LEP cells (derived from a 66-year old woman, strain 237) that were FACS-enriched ahead of mechano-NPS characterization. Although LEP cells, on average, had a similar transverse deformation as that of MEP cells, they required less time to pass through the contraction channel, thus suggesting that they are more deformable to an applied strain in the channel-width direction. Furthermore, while the deformed diameter and transit time of both lineages are dependent on the free cellular diameter, there are clear differences between the wCDI distribution of MEP ($\overline{wCDI}$=0.865±0.107) and LEP ($\overline{wCDI}$=1.133±0.144) cells. In terms of cell recovery, MEP and LEP cells show a similar distribution of recovery types.

We also measured the mechanical properties of primary HMEC cultures that consisted of mixtures of MEP and LEP cells from eight women of different chronological age (four pre-menopausal women aged <30 y and four post-menopausal women aged >55 y). Using the Expectation-Maximization algorithm[80], in which the wCDI distribution function of sorted MEP and LEP cells obtained in our earlier experiments were used as initial values, we determined the ratio (α) of MEP and LEP cells within each primary HMEC strain (and subsequently compared this ratio to FACS analysis of CD10+/CD227− MEP and CD10−/CD227+ LEP. The component ratios of MEP and LEP cells, as determined by the wCDI distributions, match exceptionally well with those obtained from FACS, as confirmed by a chi-square test with a p-value=0.05. Indeed, the two methods are statistically indistinguishable. Although age-dependent differences in wCDI were not detected, age-dependent differences were readily apparent in recovery. Our data also show the composition of cell-recovery type for MEP and LEP cells of the young and old HMEC strains. Younger HMEC strains strikingly have a higher proportion of cells that recover instantaneously (an average of 47.8%) as compared to older strains (an average of 19.9%), suggesting that the cytoskeleton in younger cells is more resilient or more active, and in turn more responsive, to mechanical deformation.

We next determined whether HMEC traversing the stages of malignant progression have distinctive mechanical signatures that could be used to track these stages. We previously reported a method for producing post-stasis and immortal HMEC cell lines in the absence of gross, and confounding, genomic errors[81]. In this experiment, expression of p16 shRNA or cyclin D1 was used to bypass the stress-induced stasis barrier, and expression of c-myc was used to bypass the replicative senescence barrier and generate immortal non-malignant cell lines. We used mechano-NPS to generate wCDI profiles and the recovery-type distribution of primary normal HMEC strains (240L and 122L), post-stasis finite strains (240L-p16sh, 240L-D1, 122L-p16sh, 122L-D1,), and immortal non-malignant cell lines (240Lp16sMY, 240LD1MY, 122Lp16sMY, 122LD1MY). Each stage of malignant progression had a unique wCDI distribution. 240LD1MY, 122LD1MY, and 122Lp16sMY are known to have molecular and biochemical signatures of the luminal cancer subtype[82]. Their wCDI profiles show a mean that is greater than those of their normal isogenic HMEC predecessors, which also is consistent with a more LEP phenotype. In contrast, 240p16sMY have a molecular and biochemical phenotype of basal breast cancers, which bear more similarity to MEP than to LEP lineage, and the wCDI distribution was more consistent with that of MEP. The post-stasis finite strains exhibited wCDI distributions that were intermediate phenotypes between normal HMEC and the isogenic immortal malignant cell lines, in a manner consistent with the eventual intrinsic luminal- or basal-like subtype of the immortal lines. Interestingly, all immortal non-malignant cell lines screened have a greater fraction of cells that exhibit instant or transient recovery as compared to those of post-stasis finite strains. When comparing the older pre-stasis strain, 122L to the isogenic immortal cell lines, there was a particularly stark decrease in recovery time. Thus, we observed two different types of mechanical signatures: wCDI differed between the MEP and LEP lineages, whereas recovery from deformation was a distinguishing characteristic of chronological age. Moreover, these data provide functional evidence to suggest that the process of immortalization is associated with fundamental changes in the ability of cytoskeletons to respond to deformation.

Discussion

Mechano-NPS is a versatile technique that can analyze populations of single cells for a number of biophysical properties, simultaneously. Our newly defined dimensionless parameter, wCDI, which corresponds to whole-cell deformability, allows us to compare different cell types directly. Complementing the wCDI, the quantification of the cellular deformation in the transverse direction when cells are subject to compressive deformation, cell recovery from deformation, and the subsequent distribution of different cell-recovery types provide unique information about a cell population. Utilizing just these three parameters, we have shown stark differences between, and even patterns of cell recovery among, malignant and non-malignant cells, sub-lineages and chronological age groups, along with changes in the cytoskeleton. In general, the multi-variable phenotyping achieved by mechano-NPS provides a comprehensive understanding of single-cell mechanical behavior. Hierarchical clustering analysis of the NPS-screened mechanical phenotypes demonstrates a relationship among specific mechanical phenotypes with respect to different cell lines and with respect to the malignant progression of HMECs (Supplementary FIGS. 11 and 12). Single-cell level mechano-profiling enables the identification of rare and/or masked sub-populations that comprise a bulk cell population, as well as characterization of cell states during dynamics processes—not just those studied here—solely based on mechanical phenotype.

While we have focused on the wCDI, transverse deformation, and cell recovery here, additional biophysical parameters can be measured with mechano-NPS simply by adding more node-pore sequences, which would, for instance, increase the time resolution needed for investigating the mechanical plasticity of cells. We can also utilize different contraction channel geometries. For example, employing a sinusoidal contraction channel induces periodic deformation to probe cellular viscoelastic properties, which depend non-linearly on the frequency of deformation. Taken together, the many biophysical properties that can be measured with mechano-NPS provides better understanding of the origins of specific cellular mechanical properties and the mechanical contributions of different cellular components (e.g. cytoskeleton, nuclear envelope, organelles, and their own associated non-linear properties). In general nechano-NPS mechanically phenotypes cells for identification. Additional attractive features of mechano-NPS include that it is label-free, screened cells remain viable, and the ability to couple this technique with microfluidic cell-sorting technologies. We screened up to 350 cells/min with our mechano-NPS device in the experiments we have presented. Because of the overall length of the channel, coincidence events, in which more than one cell occupies the channel at any given time, occur on occasion, especially when screening a high concentration of cells. Because of their complexity, current pulses arising from these events are presently removed from analysis. Implementing advanced signal processing, such as match filtering, can deconvolve these particular pulses and substantially increase throughput by enabling higher flow rate and higher concentration of cells[83, 84]. Although it currently has significantly lower throughput compared to hydrodynamic stretching cytometry[27], deformability cytometry[31, 32], and RT-DC[30], mechano-NPS does not rely on optical imaging and therefore can easily be scaled up. Many mechano-NPS channels can be operated in parallel, resulting in overall increased throughput (on the order of many thousands of cells/min), while importantly still maintaining the ability to examine cell recovery. Equally important, the simplicity of mechano-NPS, even in multiplexed form, is preserved.

Cellular mechanical properties can reflect malignancy of cancer cells and their metastatic potential[85]. Mechano-NPS reveals and quantifies emergent functional properties of the cytoskeleton of cells. Consequently, mechano-NPS can evaluate cytoskeleton-targeted drugs (e.g. estramustine, colchicine, and paclitaxel), which are often employed in cancer therapies[86, 87], and provides a new platform for analyzing drug resistance of cancer cells, which can be caused in part by their cytoskeletal components[88, 89]. The ability of our platform to rapidly characterize mechanical properties in populations of cells provides numerous practical applications. For example, mechano-NPS can be used to assay rapidly common laboratory cell lines cultured under different conditions and confluences, and to determine whether cells coming out of culture are in a similar state from day-to-day. Clinically, mechano-NPS provides a new approach to early detection of breast and other types of cancer genesis through analyzing epithelial cells and their composition ratio. Indeed, we have already demonstrated mechano-NPS's ability to distinguish between LEP and MEP lineages in mixed populations, between epithelial cells from pre- or post-menopausal women, and between normal and immortal transformed epithelial cells from the same individual. The proportions of MEP and LEP subpopulations in mammary epithelium is highly associated with age of women[47], and when combined with distinct deformation recovery phenotypes in normal and transformed cells, mechano-NPS provides valuable information regarding risk or diagnosis of breast cancer. We previously reported that the intrinsic subtype of immortal transformed HMEC was observable at the earliest stage of progression, bypass of stress-induced stasis, using molecular and biochemical markers of lineage. Here, we show that the stage of progression and the intrinsic subtypes are associated with distinctive mechanical phenotypes, opening up the possibility that wCDI could be used in a diagnostic setting as well.

Mechano-NPS is a multi-parametric, electronic-based, single-cell analysis method that can quantify cell diameter, resistance to compressive deformation, transverse deformation under constant strain, and recovery time after deformation, simultaneously. As demonstrated, the newly defined index wCDI, transverse deformation, and recovery time provide a quantitative mechanical metric for discriminating among different cell types, identifying sub-lineages of primary human mammary epithelial cells, and analyzing phenotypes that correlate with chronological age and malignant progression of human mammary epithelial cells. Mechano-NPS thus has great potential to be utilized as an efficient, label-free mechanical phenotyping tool for basic and clinical applications requiring characterization of cellular mechanics at the single-cell level.

PDMS Embodiment

Figures 8A, 8B:
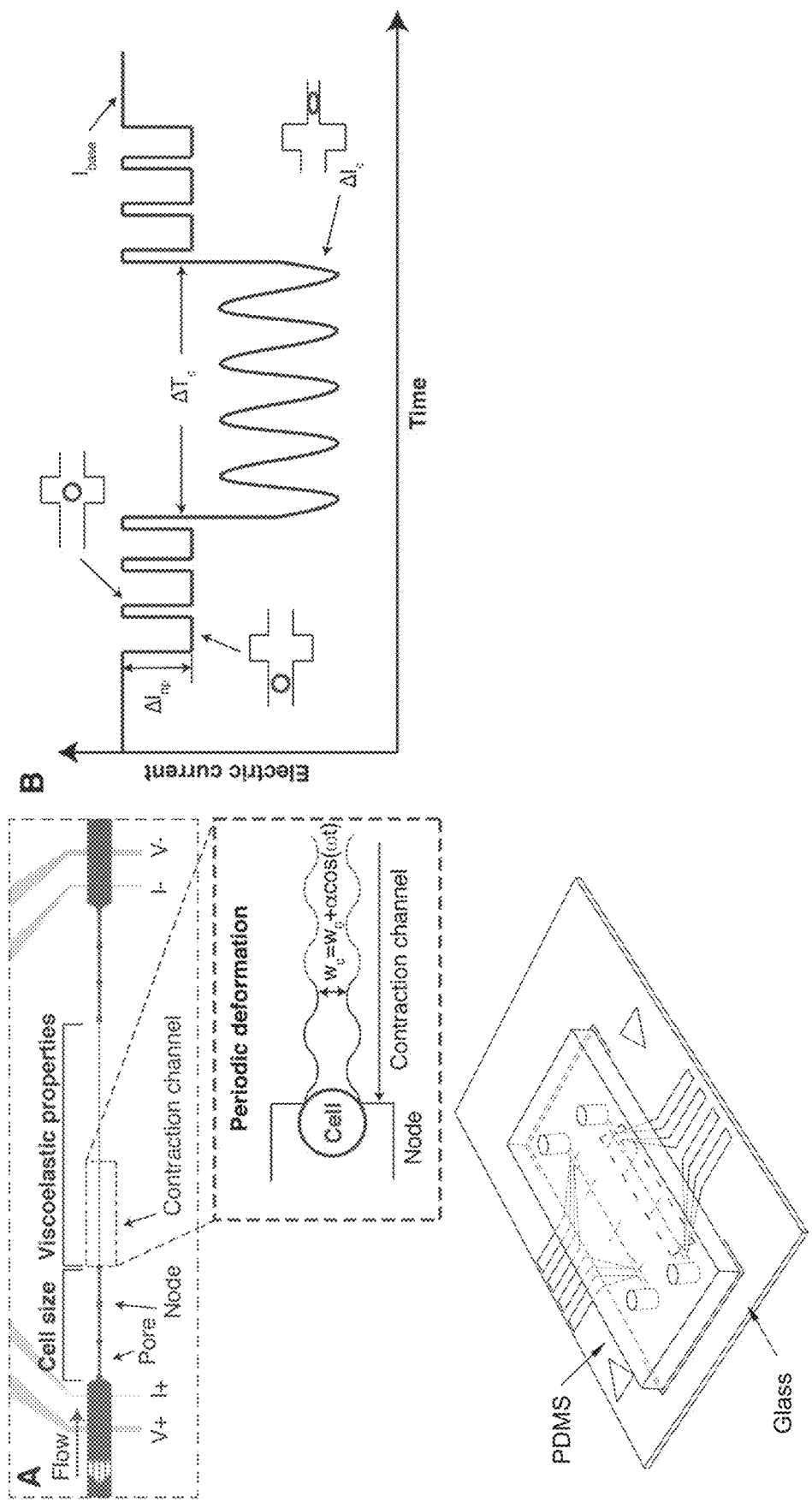
FIG. 8A-8B. Microfluidic rheometry. a, Dashed box (top) shows the overall structure of the microfluidic channel; dashed box (bottom right) shows an enlarged view of the contraction channel with its periodically changing channel width ($w_c$). b, Expected current pulse produced by a cell transiting the microfluidic channel.

In an embodiment our microfluidic rheometer comprises a polydimethylsiloxane (PDMS) mold bonded to a glass substrate with pre-defined platinum electrodes. Embedded in the mold is a microfluidic channel with three major components: nodes, pores, and a contraction channel (FIG. 8A). While a node-pore sequence determines cell size (Balakrishnan, K. R. et al. Node-Pore Sensing Enables Label-Free Surface-Marker Profiling of Single Cells. Analytical chemistry 87, 2988-2995 (2015), the contraction channel, with its sinusoidal geometry that deforms a cell in an oscillatory manner, measures cell viscoelastic properties. To demonstrate the power of our platform, we measured malignant (MCF7) and non-malignant (MCF10A) breast epithelial cells. We used a non-pulsatile pressure ($P_{inlet}$=14~32 kPa) to drive cells through our device, and we performed a four-terminal measurement of the current across the entire microfluidic channel when we applied a 1V DC voltage. As a cell traversed the channel, we measured a unique current pulse (FIG. 8B). In general, cell diameter ($D_{cell}$) and deformed diameter ($D_{deform}$) correspond to the current drop magnitude at the node-pore ($\Delta I_{np}$) and at the contraction channel ($\Delta I_c$), respectively. The transit time ($\Delta T_c$) required for a cell to traverse through the contraction region is reflected in the pulse duration. From $\Delta T_c$, we quantify the applied deformation frequency, $\omega$=the number of cycles/$\Delta T_c$.

By adjusting $P_{inlet}$, we can vary $\omega$, which in turn enables us to analyze the frequency-dependent viscoelastic response of a cell. Using the measured parameters ($D_{cell}$, $D_{deform}$, $\omega$) in the force balance equations of a deformed cell in the contraction channel, we calculate the storage (G') and loss (G") modulus of a cell. Overall, we found that MCF10A cells have a larger G' and G" compared to those of MCF7 cells, implying that they are stiffer and more viscous. Importantly, the fitted power-law structural damping model shows that G' and G" of MCF10A cells increase with w more rapidly than those of MCF7 cells. Our results indicate that there is a significant difference between the viscoelastic response of malignant MCF7 and non-malignant MCF-10A cells. This finding can be used to evaluate the metastatic or invasive potential of cancer cells.

Detailed Description of the Drawings

FIG. 1A-1D. Principle of mechanical phenotyping via mechano-NPS. a, A photographic image of the microfluidic platform. The scale bar corresponds to 4 mm. Dashed box shows a close-up view of the entire microfluidic channel. The microfluidic channel (pore) is segmented by nodes and a contraction channel. Two electrodes at both ends of the channel apply a constant voltage (1V), and two inner electrodes measure the change of current across the channel. The regions where free-cell diameter, deformed diameter, and cell recovery are measured are as indicated. b, Expected current pulse generated by a cell transiting the microfluidic channel. I, $\Delta I_{np}$, $\Delta I_c$, and $\Delta I_r$ correspond to the baseline current and the current drop by a cell transiting a node-pore, a contraction channel, and a node-pore after the contraction channel, respectively. Numbers in parentheses (1-4) correspond to the same specific segments of the microchannel (pore, node, and contraction channel) in a. $\Delta T_{cont}$ corresponds to the time duration of a cell passing through the contraction channel, and $\Delta T_r$ indicates the time needed for $\Delta I_r$ to equal $\Delta I_{np}$. (inset) An actual current pulse caused by a human mammary epithelial cell traversing the channel. c, Time-snapshots of an MCF-7 cell (bordered by a white circle) in each of the different segments of the microfluidic channel (white dashed line). Numbers in parentheses (1-4) correspond to the same specific segments of the microchannel (pore, node, and contraction channel) in a. d, Cross-sectional diagram of the channel segments occupied by a cell. 'AA' and 'BB' indicate the corresponding cross-sections in c. $w_{pore}$, $w_{node}$, $w_c$, and $h_{channel}$ correspond to the widths of the pore, node, and the contraction channel, and the height of the channel, respectively. $D_{cell}$ and $L_{deform}$ correspond to the free-cell diameter in the node-pore channel and the elongated length of the deformed cell in the contraction channel, respectively.

FIG. 2. The electrical circuit model for the constant voltage four-point measurement[1, 2]. The dashed box represents the impedances of the electrode, fluid, and cell of the microfluidic device (Mechano-NPS). $R_f$ and $C_f$ represent the circuit elements. $R_p$ and $C_p$ indicate the resistance and capacitance of the microfluidic channel and $R_H$ and $R_L$ represent the resistance of the fluid in the inlet and outlet reservoir. Through the first amplifier (INA100), the output is a sum of the voltage difference across the microfluidic channel ($V_H$–$V_L$) and the input voltage, $V_{in}$. This becomes the inverting input for the second amplifier (OP27). Through this feedback arrangement, the current flows from $I_H$ to $I_L$ and then to $I_{out}$ (arrows).

FIG. 3A-E. Signal processing by customized MATLAB code. The acquired signal a, is first low-pass filtered b, to remove noise. The base-line is then normalized c, to remove any drift. d, A derivative cut-off detection is subsequently employed as an index to determine the start and end point of each pulse. e, Finally, the current pulse magnitude and duration are measured based on this index.

FIG. 4. wCDI of MCF7 cells from different replicas of the mechano-NPS device. MCF7 cells were measured by different replica of the device showing no statistical difference (MCF-7(1): n=97, MCF-7(2): n=99, p=0.173). The statistical difference was determined by a paired t-test. Within each box, the central line is the median and the edges of the box correspond to 25% and 75% of the wCDI distribution.

Figures 5A, 5B, 5C:
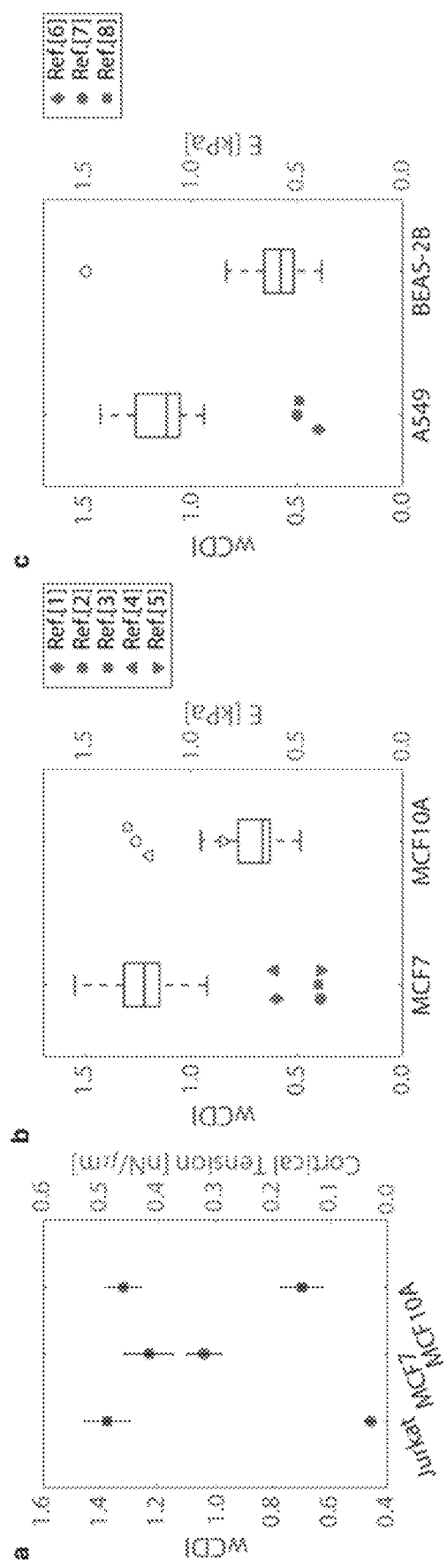
FIG. 5A-5C. Relationship between mechanical properties and wCDI. a, Comparison of wCDI with cortical tension as determined by micropipette aspiration of Jurkat, MCF7, and MCF10A cells. Comparison of wCDI with the elastic modulus, as measured by AFM, of breast cell lines (b) and lung cell lines (c).

FIG. 5A-5C. Relationship between mechanical properties and wCDI. a, Comparison of wCDI with cortical tension as determined by micropipette aspiration of Jurkat, MCF7, and MCF10A cells. The wCDI is inversely related to cortical tension. Error bar indicates standard deviation for wCDI and standard error for cortical tension. b and c, Comparison of wCDI with the elastic modulus, as measured by AFM, of breast cell lines (b) and lung cell lines (c). Within each box, the central line is the median and the edges of the box correspond to 25% and 75% of the wCDI distribution. The symbols are the reported elastic modulus of each cell line[3-10]. The trend of wCDI over various cell lines is inversely proportional to the elastic modulus.

FIG. 6. Computational modeling of the electric field when a cell transits each section of the mechano-NPS microfluidic channel. The fine lines correspond to the calculated electric-field lines in each section of the microfluidic channel, and the white circle corresponds to a cell. As determined, the electric-field density, J, in the contraction channel is greater than that in the node. Computational simulation was performed using Comsol Multiphysics 5.0.

Figures 7A, 7B, 7C:
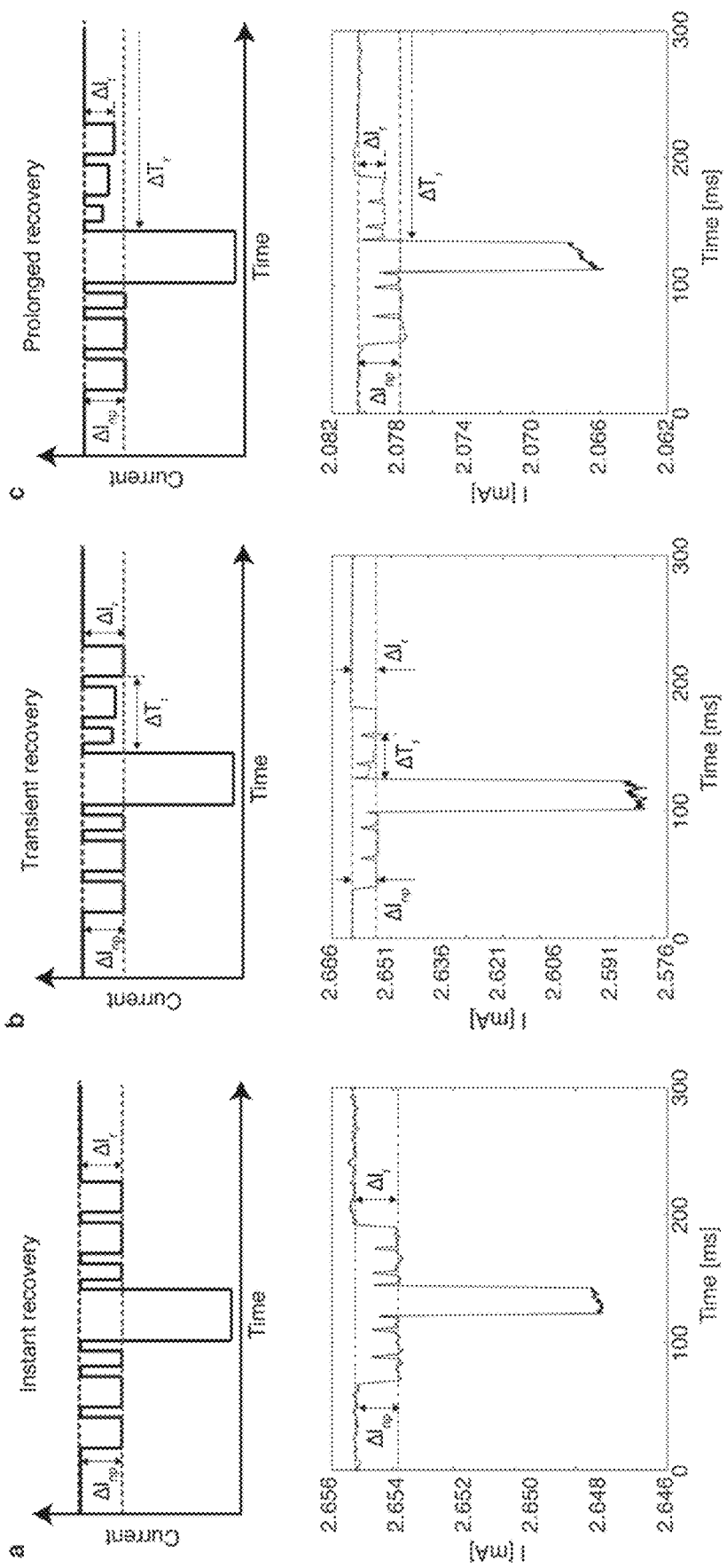
FIG. 7A-7C. Schematic and representative mechano-sensing current pulses produced by an HMEC to illustrate the defined cellular recovery types after compressive deformation: a, Instant recovery; b, Transient recovery; c, Prolonged recovery.

FIG. 7A-7C. Schematic and representative mechano-sensing current pulses produced by an HMEC to illustrate the defined cellular recovery types after compressive deformation. a, Instant recovery: The current drop (red dashed line) with respect to the baseline (dashed line) at the node-pore before and after the contraction channel are defined as $\Delta I_{np}$ and $\Delta I_r$, respectively. We define "instant recovery" when a cell recovers to its original size and shape immediately after exiting the contraction channel and $\Delta I_r = \Delta I_{np}$. In this case, $\Delta T_r \sim 0$. b, Transient recovery corresponds to the case when the cell recovers to its original size and shape, again defined as $\Delta I_r = \Delta I_{np}$, within the span of the node-pore sequence immediately following the contraction channel. Here, $\Delta T_r \leq 40$ ms. c, Prolonged recovery corresponds to the case when the cell does not recover to its original size and shape. In this specific case, $\Delta I_r \neq \Delta I_{np}$ over the time scale recorded by mechano-NPS ($\Delta T_r > 40$ ms). All schematic drawings (a, b, and c, top) show the idealized mechano-NPS current pulse. The representative current pulses (a, b, and c, bottom) show that the current at the "node" does not reach to the baseline current and has a more peak-like shape. This is due to the fast flow rate of the cells and the short length of the "node" segment.

FIG. 8A-8B. Microfluidic rheometry. a, Dashed box (top) shows the overall structure of the microfluidic channel. Dashed box (bottom right) shows an enlarged view of the contraction channel with its periodically changing channel width ($w_c$). b, Expected current pulse produced by a cell transiting the microfluidic channel. $I_{base}$, $\Delta I_{np}$, $\Delta I_c$, and $\Delta T_c$ correspond to the baseline current, the current drop at the node-pore, the oscillating current drop at the contraction channel, and the time duration of a cell traversing through the contraction channel.

REFERENCES

1. Swaminathan V, Mythreye K, O'Brien E T, Berchuck A, Blobe G C, Superfine R. Mechanical stiffness grades metastatic potential in patient tumor cells and in cancer cell lines. Cancer research 2011; 71(15): 5075-5080.
2. Xu W, Mezencev R, Kim B, Wang L, McDonald J, Sulchek T. Cell stiffness is a biomarker of the metastatic potential of ovarian cancer cells. PloS one 2012; 7(10): e46609.
3. Brunet S, Maro B. Cytoskeleton and cell cycle control during meiotic maturation of the mouse oocyte: integrating time and space. Reproduction 2005; 130(6): 801-811.
4. Needham D. Possible role of cell cycle-dependent morphology, geometry, and mechanical properties in tumor cell metastasis. Cell biophysics 1991; 18(2): 99-121.
5. Mundel P, Reiser J, Borja AZMa, Pavenstädt H, Davidson G R, Kriz W, et al. Rearrangements of the cytoskeleton and cell contacts induce process formation during differentiation of conditionally immortalized mouse podocyte cell lines. Experimental cell research 1997; 236(1): 248-258.
6. González-Cruz R D, Fonseca V C, Darling E M. Cellular mechanical properties reflect the differentiation potential of adipose-derived mesenchymal stem cells. Proceedings of the National Academy of Sciences 2012; 109(24): E1523-E1529.
7. Darling E M, Di Carlo D. High-throughput assessment of cellular mechanical properties. Annual review of biomedical engineering 2015; 17: 35-62.
8. Bagnall J S, Byun S, Miyamoto D T, Kang J H, Maheswaran S, Stott S L, et al. Deformability-based cell selection with downstream immunofluorescence analysis. Integrative Biology 2016; 8(5): 654-664.
9. Bongiorno T, Chojnowski J L, Lauderdale J D, Sulchek T. Cellular stiffness as a novel stemness marker in the corneal limbus. Biophysical journal 2016; 111(8): 1761-1772.
10. Lee W C, Shi H, Poon Z, Nyan L M, Kaushik T, Shivashankar G, et al. Multivariate biophysical markers predictive of mesenchymal stromal cell multipotency. Proceedings of the National Academy of Sciences 2014; 111(42): E4409-E4418.
11. Cerchiari A E, Garbe J C, Jee N Y, Todhunter M E, Broaders K E, Peehl D M, et al. A strategy for tissue self-organization that is robust to cellular heterogeneity and plasticity. Proceedings of the National Academy of Sciences 2015; 112(7): 2287-2292.
12. Zheng Y, Nguyen J, Wei Y, Sun Y. Recent advances in microfluidic techniques for single-cell biophysical characterization. Lab on a Chip 2013; 13(13): 2464-2483.
13. Kirschenbaum L A, Aziz M, Astiz M E, Saha D C, Rackow E C. Influence of rheologic changes and platelet-neutrophil interactions on cell filtration in sepsis. American journal of respiratory and critical care medicine 2000; 161(5): 1602-1607.
14. Starodubtseva M N. Mechanical properties of cells and ageing. Ageing Research Reviews 2011 1//; 10(1): 16-25.
15. Li Q, Lee G, Ong C, Lim C. AFM indentation study of breast cancer cells. Biochemical and biophysical research communications 2008; 374(4): 609-613.
16. Zhou Z, Zheng C, Li S, Zhou X, Liu Z, He Q, et al. AFM nanoindentation detection of the elastic modulus of tongue squamous carcinoma cells with different metastatic potentials. Nanomedicine: Nanotechnology, Biology and Medicine 2013; 9(7): 864-874.
17. Rother J, Nöding H, Mey I, Janshoff A. Atomic force microscopy-based microrheology reveals significant differences in the viscoelastic response between malign and benign cell lines. Open biology 2014; 4(5): 140046.
18. Hochmuth R M. Micropipette aspiration of living cells. Journal of biomechanics 2000; 33(1): 15-22.
19. Hogan B, Babataheri A, Hwang Y, Barakat A I, Husson J. Characterizing Cell Adhesion by Using Micropipette Aspiration. Biophysical journal 2015; 109(2): 209-219.

20. Lee L M, Liu A P. The application of micropipette aspiration in molecular mechanics of single cells. Journal of nanotechnology in engineering and medicine 2014; 5(4): 040902.
21. Lee L M, Liu A P. A microfluidic pipette array for mechanophenotyping of cancer cells and mechanical gating of mechanosensitive channels. Lab on a Chip 2015; 15(1): 264-273.
22. Wang A, Vijayraghavan K, Solgaard O, Butte M J. Fast stiffness mapping of cells using high-bandwidth atomic force microscopy. ACS nano 2015; 10(1): 257-264.
23. Li J, Dao M, Lim C, Suresh S. Spectrin-level modeling of the cytoskeleton and optical tweezers stretching of the erythrocyte. Biophysical Journal 2005; 88(5): 3707-3719.
24. Planus E, Fodil R, Balland M, Isabey D. Assessment of mechanical properties of adherent living cells by bead micromanipulation: comparison of magnetic twisting cytometry vs optical tweezers. Journal of biomechanical engineering 2002; 124(4): 408-421.
25. Thoumine O, Ott A, Cardoso O, Meister J-J. Microplates: a new tool for manipulation and mechanical perturbation of individual cells. Journal of biochemical and biophysical methods 1999; 39(1): 47-62.
26. De Vlaminck I, Valantine H A, Snyder T M, Strehl C, Cohen G, Luikart H, et al. Circulating cell-free DNA enables noninvasive diagnosis of heart transplant rejection. Science translational medicine 2014; 6(241): 241ra277-241ra277.
27. Gossett D R, Henry T, Lee S A, Ying Y, Lindgren A G, Yang O O, et al. Hydrodynamic stretching of single cells for large population mechanical phenotyping. Proceedings of the National Academy of Sciences 2012; 109(20): 7630-7635.
28. Dudani J S, Gossett D R, Henry T, Di Carlo D. Pinched-flow hydrodynamic stretching of single-cells. Lab on a Chip 2013; 13(18): 3728-3734.
29. Byun S, Son S, Amodei D, Cermak N, Shaw J, Kang J H, et al. Characterizing deformability and surface friction of cancer cells. Proceedings of the National Academy of Sciences 2013; 110(19): 7580-7585.
30. Otto O, Rosendahl P, Mietke A, Golfier S, Herold C, Klaue D, et al. Real-time deformability cytometry: on-the-fly cell mechanical phenotyping. nature methods 2015; 12(3): 199-202.
31. Masaeli M, Gupta D, O'Byrne S, Henry T, Gossett D R, Tseng P, et al. Multiparameter mechanical and morphometric screening of cells. Scientific reports 2016; 6: 37863.
32. Lin J, Kim D, Henry T T, Tseng P, Peng L, Dhar M, et al. High-throughput physical phenotyping of cell differentiation. Microsystems & Nanoengineering 2017; 3: 17013.
33. Wirtz D, Konstantopoulos K, Searson P C. The physics of cancer: the role of physical interactions and mechanical forces in metastasis. Nature Reviews Cancer 2011; 11(7): 512-522.
34. Bonakdar N, Gerum R, Kuhn M, Spörrer M, Lippert A, Schneider W, et al. Mechanical plasticity of cells. Nature Materials 2016.
35. Trickey W R, Baaijens F P, Laursen T A, Alexopoulos L G, Guilak F. Determination of the Poisson's ratio of the cell: recovery properties of chondrocytes after release from complete micropipette aspiration. Journal of biomechanics 2006; 39(1): 78-87.
36. Ofek G, Wiltz D C, Athanasiou K A. Contribution of the cytoskeleton to the compressive properties and recovery behavior of single cells. Biophysical journal 2009; 97(7): 1873-1882.
37. Balakrishnan K R, Anwar G, Chapman M R, Nguyen T, Kesavaraju A, Sohn L L. Node-pore sensing: a robust, high-dynamic range method for detecting biological species. Lab on a Chip 2013; 13(7): 1302-1307.
38. Balakrishnan K R, Whang J C, Hwang R, Hack J H, Godley L A, Sohn L L. Node-Pore Sensing Enables Label-Free Surface-Marker Profiling of Single Cells. Analytical chemistry 2015; 87(5): 2988-2995.
39. Saleh O, Sohn L. Quantitative sensing of nanoscale colloids using a microchip Coulter counter. Review of Scientific Instruments 2001; 72(12): 4449-4451.
40. Saleh O A, Sohn L L. Direct detection of antibody-antigen binding using an on-chip artificial pore. Proceedings of the National Academy of Sciences 2003; 100(3): 820-824.
41. Chow S-C, Wang H, Shao J. Sample size calculations in clinical research. CRC press, 2007.
42. Freshney R I. Culture of specific cell types. Wiley Online Library, 2005.
43. ATCC. Jurkat, Clone E6-1 (ATCC® TIB-152™). [cited; Available from: https://www.atcc.org/Products/All/TIB-152.aspx
44. Sugarman B J, Aggarwal B B, Hass P E, Figari I S, Palladino M A, Shepard H M. Recombinant human tumor necrosis factor-alpha: effects on proliferation of normal and transformed cells in vitro. Science 1985; 230(4728): 943-945.
45. Giard D J, Aaronson S A, Todaro G J, Arnstein P, Kersey J H, Dosik H, et al. In Vitro Cultivation of Human Tumors: Establishment of Cell Lines Derived From a Series of Solid Tumors 2. Journal of the National Cancer Institute 1973; 51(5): 1417-1423.
46. Reddel R R, Yang K, Rhim J S, Brash D, Su R T, Lechner J F, et al. Immortalized human bronchial epithelial mesothelial cell lines. Google Patents; 1989.
47. Garbe J C, Pepin F, Pelissier F, Sputova K, Fridriksdottir A J, Guo D E, et al. Accumulation of multipotent progenitors with a basal differentiation bias during aging of human mammary epithelia. Cancer Research 2012 05/02; 72(14): 3687-3701.
48. LaBarge M A, Garbe J C, Stampfer M R. Processing of human reduction mammoplasty and mastectomy tissues for cell culture. JoVE (Journal of Visualized Experiments) 2013; (71): e50011-e50011.
49. LaBarge M A. Human Mammary Epithelial Cell (HMEC) Bank Website. 2003 [cited; Available from: http://hmec.lbl.gov/mindex.html
50. Wakatsuki T, Schwab B, Thompson N C, Elson E L. Effects of cytochalasin D and latrunculin B on mechanical properties of cells. Journal of cell science 2001; 114(5): 1025-1036.
51. Coué M, Brenner S L, Spector I, Korn E D. Inhibition of actin polymerization by latrunculin A. FEBS letters 1987; 213(2): 316-318.
52. Morton W M, Ayscough K R, McLaughlin P J. Latrunculin alters the actin-monomer subunit interface to prevent polymerization. Nature cell biology 2000; 2(6): 376-378.
53. Misic T, Najdanovic-Lukic M, Nesic L. Dimensional analysis in physics and the Buckingham theorem. European Journal of Physics 2010; 31(4): 893.

54. Schiffhauer Eric S, Luo T, Mohan K, Srivastava V, Qian X, Griffis Eric R, et al. Mechanoaccumulative Elements of the Mammalian Actin Cytoskeleton. Current Biology.
55. Srivastava V, Robinson Douglas N. Mechanical Stress and Network Structure Drive Protein Dynamics during Cytokinesis. Current Biology 2015; 25(5): 663-670.
56. Schiffhauer E S, Luo T, Mohan K, Srivastava V, Qian X, Griffis E R, et al. Mechanoaccumulative elements of the mammalian actin cytoskeleton. Current Biology 2016; 26(11): 1473-1479.
57. DeBlois R, Bean C. Counting and sizing of submicron particles by the resistive pulse technique. Review of Scientific Instruments 1970; 41(7): 909-916.
58. Saleh O A. A novel resistive pulse sensor for biological measurements. Princeton University, Princeton, PhD Thesis 2003.
59. Bathe M, Shirai A, Doerschuk C M, Kamm R D. Neutrophil transit times through pulmonary capillaries: the effects of capillary geometry and fMLP-stimulation. Biophysical journal 2002; 83(4): 1917-1933.
60. Rosenbluth M, Lam W, Fletcher D. Analyzing cell mechanics in hematologic diseases with microfluidic biophysical flow cytometry. Lab on a chip 2008; 8(7): 1062.
61. Nyberg K D, Scott M B, Bruce S L, Gopinath A B, Bikos D, Mason T G, et al. The physical origins of transit time measurements for rapid, single cell mechanotyping. Lab on a Chip 2016; 16(17): 3330-3339.
62. Dokukin M E, Guz N V, Sokolov I. Quantitative study of the elastic modulus of loosely attached cells in AFM indentation experiments. Biophysical journal 2013; 104 (10): 2123-2131.
63. Li Q, Lee G, Ong C, Lim C. Probing the elasticity of breast cancer cells using AFM. 13th International Conference on Biomedical Engineering; 2009: Springer; 2009. p. 2122-2125.
64. Xu C, Wang Y, Jiang N, Yang H, Lin J, Xie S. Elasticity measurement of breast cancer cells by atomic force microscopy. Twelfth International Conference on Photonics and Imaging in Biology and Medicine (PIBM 2014); 2014: International Society for Optics and Photonics; 2014. p. 92300Y-92300Y-92306.
65. Alcaraz J, Buscemi L, Grabulosa M, Trepat X, Fabry B, Farré R, et al. Microrheology of human lung epithelial cells measured by atomic force microscopy. Biophysical journal 2003; 84(3): 2071-2079.
66. Acerbi I, Luque T, Giménez A, Puig M, Reguart N, Farré R, et al. Integrin-specific mechanoresponses to compression and extension probed by cylindrical flat-ended AFM tips in lung cells. PLoS One 2012; 7(2): e32261.
67. Demichelis A, Divieto C, Mortati L, Sassi M, Sassi G. Preliminary measurements of elasticity properties of lung tumor living cells for cancer detection. Medical Measurements and Applications (MeMeA), 2015 IEEE International Symposium on; 2015: IEEE; 2015. p. 240-243.
68. Liu A Y, Roudier M P, True L D. Heterogeneity in primary and metastatic prostate cancer as defined by cell surface CD profile. The American journal of pathology 2004; 165(5): 1543-1556.
69. Symmans W F, Liu J, Knowles D M, Inghirami G. Breast cancer heterogeneity: evaluation of clonality in primary and metastatic lesions. Human pathology 1995; 26(2): 210-216.
70. Dexter D L, Spremulli E N, Fligiel Z, Barbosa J A, Vogel R, VanVoorhees A, et al. Heterogeneity of cancer cells from a single human colon carcinoma. The American journal of medicine 1981; 71(6): 949-956.
71. Polyak K. Heterogeneity in breast cancer. The Journal of clinical investigation 2011; 121(10): 3786-3788.
72. Fisher R, Pusztai L, Swanton C. Cancer heterogeneity: implications for targeted therapeutics. British journal of cancer 2013; 108(3): 479-485.
73. Chang J C, Brewer G J, Wheeler B C. A modified microstamping technique enhances polylysine transfer and neuronal cell patterning. Biomaterials 2003; 24(17): 2863-2870.
74. Wang L, Sun B, Ziemer K S, Barabino G A, Carrier R L. Chemical and physical modifications to poly (dimethylsiloxane) surfaces affect adhesion of Caco-2 cells. Journal of biomedical materials research Part A 2010; 93(4): 1260-1271.
75. Zhou J, Ellis A V, Voelcker N H. Recent developments in PDMS surface modification for microfluidic devices. Electrophoresis 2010; 31(1): 2-16.
76. Ronan W, Deshpande V S, McMeeking R M, McGarry J P. Numerical investigation of the active role of the actin cytoskeleton in the compression resistance of cells. Journal of the Mechanical Behavior of Biomedical Materials 2012; 14: 143-157.
77. Gudjonsson T, Adriance M C, Sternlicht M D, Petersen O W, Bissell M J. Myoepithelial cells: their origin and function in breast morphogenesis and neoplasia. Journal of mammary gland biology and neoplasia 2005; 10(3): 261-272.
78. Ewald A J, Brenot A, Duong M, Chan B S, Werb Z. Collective epithelial migration and cell rearrangements drive mammary branching morphogenesis. Developmental cell 2008; 14(4): 570-581.
79. Mammoto A, Ingber D E. Cytoskeletal control of growth and cell fate switching. Current opinion in cell biology 2009; 21(6): 864-870.
80. MacKeown P K. Stochastic Simulation in Physics, 1997. Springer, Singapore, 1997.
81. Garbe J C, Vrba L, Sputova K, Fuchs L, Novak P, Brothman A R, et al. Immortalization of normal human mammary epithelial cells in two steps by direct targeting of senescence barriers does not require gross genomic alterations. Cell Cycle 2014; 13(21): 3423-3435.
82. Lee J K, Garbe J C, Vrba L, Miyano M, Futscher B W, Stampfer M R, et al. Age and the means of bypassing stasis influence the intrinsic subtype of immortalized human mammary epithelial cells. Frontiers in cell and developmental biology 2015; 3.
83. Rivest F, Pachacek A, Pack R, Goodman K, Cho N, Lustig M, et al. Toward Real-time Cell Detection and Characterization Using Barker-coded Node-pore Sensing (NPS). Proceedings of the 2015 µTAS Conference, Gyeongju, Korea; 2015; 2015. p. 47-50.
84. Kellman M, Rivest F, Pachacek A, Sohn L, Lustig M. Barker-Coded node-pore resistive pulse sensing with built-in coincidence correction. Acoustics, Speech and Signal Processing (ICASSP), 2017 IEEE International Conference on; 2017: IEEE; 2017. p. 1053-1057.
85. Kumar S, Weaver V M. Mechanics, malignancy, and metastasis: the force journey of a tumor cell. Cancer and Metastasis Reviews 2009; 28(1-2): 113-127.
86. Kavallaris M. Microtubules and resistance to tubulin-binding agents. Nature Reviews Cancer 2010; 10(3): 194-204.
87. Pasquier E, Kavallaris M. Microtubules: a dynamic target in cancer therapy. IUBMB life 2008; 60(3): 165-170.

88. De Donato M, et al. Class III β-tubulin and the cytoskeletal gateway for drug resistance in ovarian cancer. Journal of cellular physiology 2012; 227(3): 1034-1041.
89. Bichat F, et al. Cytoskeleton alteration in MCF7R cells, a multidrug resistant human breast cancer cell line. Anticancer research 1996; 17(5A): 3393-3401.

SUPPLEMENTARY REFERENCES

1. Saleh O A. A novel resistive pulse sensor for biological measurements. Princeton University, Princeton, PhD Thesis 2003.
2. Carbonaro A, Sohn L. A resistive-pulse sensor chip for multianalyte immunoassays. Lab on a Chip 2005; 5(10): 1155-1160.
3. Dokukin M E, Guz N V, Sokolov I. Quantitative study of the elastic modulus of loosely attached cells in AFM indentation experiments. Biophysical journal 2013; 104(10): 2123-2131.
4. Li Q, Lee G, Ong C, Lim C. Probing the elasticity of breast cancer cells using AFM. 13th International Conference on Biomedical Engineering; 2009: Springer; 2009. p. 2122-2125.
5. Rother J, Nöding H, Mey I, Janshoff A. Atomic force microscopy-based microrheology reveals significant differences in the viscoelastic response between malign and benign cell lines. Open biology 2014; 4(5): 140046.
6. Li Q, Lee G, Ong C, Lim C. AFM indentation study of breast cancer cells. Biochemical and biophysical research communications 2008; 374(4): 609-613.
7. Xu C, Wang Y, Jiang N, Yang H, Lin J, Xie S. Elasticity measurement of breast cancer cells by atomic force microscopy. Twelfth International Conference on Photonics and Imaging in Biology and Medicine (PIBM 2014); 2014: International Society for Optics and Photonics; 2014. p. 92300Y-92300Y-92306.
8. Alcaraz J, Buscemi L, Grabulosa M, Trepat X, Fabry B, Farré R, et al. Microrheology of human lung epithelial cells measured by atomic force microscopy. Biophysical journal 2003; 84(3): 2071-2079.
9. Acerbi I, Luque T, Giménez A, Puig M, Reguart N, Farré R, et al. Integrin-specific mechanoresponses to compression and extension probed by cylindrical flat-ended AFM tips in lung cells. PLoS One 2012; 7(2): e32261.
10. Demichelis A, Divieto C, Mortati L, Sassi M, Sassi G. Preliminary measurements of elasticity properties of lung tumor living cells for cancer detection. Medical Measurements and Applications (MeMeA), 2015 IEEE International Symposium on; 2015: IEEE; 2015. p. 240-243.

Inventor Post Priority Date Disclosures a. Junghyun Kim, Sewoon Han, and Lydia Sohn, "Microfluidic rheology to characterize viscoelastic properties of malignant and non-malignant epithelial cells", International Conference on Miniaturized System for Chemistry and Life Sciences (MicroTAS) 2017.
b. Junghyun Kim and Lydia Sohn, "Characterizing Cellular Mechanical Phenotypes with Mechano-Node-Pore Sensing", UC Berkeley Bioscience Symposium, 2017.
c. Junghyun Kim and Lydia L. Sohn, "A Microfluidic Oscillatory Rheometer to Measure Viscoelastic Properties of Cancer cells", 7th Intrnl Conf Bioengineering and Nanotechnol, 2017.
d. Lydia L. Sohn "Node-Pore Sensing: A Label-Free Platform to Screen Single Cells for their Phenotypic Profile", Dept. Biomed Engineering, Univ Oklahoma, Norman, Okla., Mar. 9, 2017.
e. Lydia L. Sohn, "Node-Pore Sensing: A Label-Free Platform to Screen Single Cells for their Phenotypic Profile", 25th Annual Conference, New England Bioscience Society, May 20, 2017
f. Lydia L. Sohn, "Node-Pore Sensing: A Versatile, Label-Free Method for Screening Single Cells", RNA-Seq, Single Cell Analysis, & Single Molecule Analysis 2017, San Diego, Calif., Oct. 5-6, 2017.

The invention claimed is:

1. A mechano-node-pore sensor comprising:
a microfluidic channel comprising a first node-pore section, a contraction channel, and a second node-pore section, and
electrodes applying a constant voltage and measuring changes in current across the microfluidic channel;
and containing a cell transiting the microfluidic channel;
wherein each node-pore section comprises a plurality of alternating nodes and pores, with the nodes wider than the pores, providing repeated expansion and contraction of a width of the microfluidic channel, so that a current pulse is generated by the cell transiting the microfluidic channel;
wherein the contraction channel is a sinusoidal contraction channel comprising a sinusoidal geometry that deforms the cell in an oscillatory manner as the cell transits the contraction channel;
wherein the mechano-node-pore sensor is configured such that upon entering the microfluidic channel, the cell partially blocks the current, and consequently, the current drops from a baseline value, and when the cell enters a first node of the first node-pore section, the current returns to the baseline value, only to drop again once the cell exits the first node, and the current rises and falls as the cell enters and exits subsequent nodes of the first node-pore section, and upon entering the contraction channel, which has a width narrower than a diameter of the cell, the cell deforms, and blocks more of the current, such that current drop from baseline is greater than that resulting from the cell transiting the pores of the first node-pore section, and after exiting the contraction channel, the cell subsequently enters and exits the nodes and the pores of the second node-pore section, wherein the cell transiting the microfluidic channel provides a unique and symmetrical shape to the current pulse, wherein the mechano-node-pore sensor provides simultaneous measurement of the cell's diameter, transit time, transverse deformation, and recovery from deformation.

2. The mechano-node-pore sensor of claim 1, wherein the contraction channel is configured to induce periodic deformation to probe cellular viscoelastic properties, which depend non-linearly on the frequency of deformation.

3. The mechano-node-pore sensor of claim 1, wherein the contraction channel has a length providing ~30 ms over which time the cell experiences constant applied strain.

4. The mechano-node-pore sensor of claim 1, wherein the cell is ~15-20 μm in diameter.

5. The mechano-node-pore sensor of claim 1, wherein the cell is a cancer cell.

6. The mechano-node-pore sensor of claim 1, further comprising a filter configured to exclude from the microfluidic channel clusters of cells that may otherwise clog the microfluidic channel.

7. The mechano-node-pore sensor of claim 1, further comprising a filter configured to exclude from the microfluidic channel clusters of cells that may otherwise clog the microfluidic channel, wherein the filter is 25 μm in width.

8. The mechano-node-pore sensor of claim 1, wherein the constant voltage is 1V.

9. The mechano-node-pore sensor of claim 1, configured to provide a whole-cell deformability index (wCDI) normalizing the effects of the cell's diameter.

10. A method of mechano-node-pore sensing, comprising using a mechano-node-pore sensor of claim 1 to measure simultaneously the cell's diameter, transit time, transverse deformation, and recovery from deformation.

* * * * *